United States Patent [19]
Niemers et al.

[11] 4,194,004
[45] Mar. 18, 1980

[54] SUBSTITUTED BENZENESULPHONIC ACID ESTERS, PROCESSES FOR THEIR PREPARATION AND THEIR USE AS MEDICAMENTS

[75] Inventors: Ekkehard Niemers; Hartmund Wollweber, both of Wuppertal; Heinrich Kölling, Haan; Herbert Thomas, Wuppertal, all of Fed. Rep. of Germany

[73] Assignee: Bayer Aktiengesellschaft, Leverkusen, Fed. Rep. of Germany

[21] Appl. No.: 847,890

[22] Filed: Nov. 2, 1977

[30] Foreign Application Priority Data

Nov. 26, 1976 [DE] Fed. Rep. of Germany ....... 2653766

[51] Int. Cl.$^2$ ................. A61K 31/27; A61K 31/255; C07C 143/68
[52] U.S. Cl. ................ 424/300; 260/397.6; 260/456 A; 424/303; 544/399; 546/232
[58] Field of Search ............ 260/456 A, 397.6; 424/303, 300

[56] References Cited
U.S. PATENT DOCUMENTS

| 3,996,368 | 12/1976 | Loewe et al. .............. 260/456 A |
| 3,996,369 | 12/1976 | Loewe et al. .............. 260/456 A |
| 4,021,571 | 5/1977 | Kolling et al. .............. 424/303 |

Primary Examiner—Nicky Chan
Attorney, Agent, or Firm—Sprung, Felfe, Horn, Lynch & Kramer

[57] ABSTRACT

Novel substituted benzenesulphonic acid esters, particularly useful as anthelmintics are provided. The novel compounds are those of the general formula

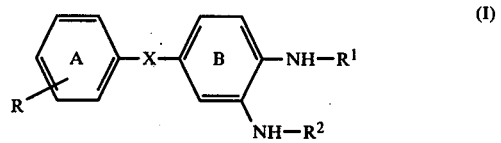

in which
R represents hydrogen, optionally substituted alkyl, cyano, alkoxy, halogen, trifluoromethyl, amino, acylamino or nitro,
X represents $SO_3$ and
$R^1$ and $R^2$ are different from one another and individually represent one of the radicals

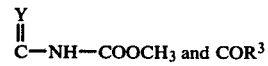

wherein
Y represents S and
$R_3$ represents hydrogen, optionally substituted alkyl or alkoxy, and salts thereof. Also included in the invention are methods for preparing the novel compounds, compositions containing them and methods for the use of the compounds and compositions.

13 Claims, No Drawings

SUBSTITUTED BENZENESULPHONIC ACID ESTERS, PROCESSES FOR THEIR PREPARATION AND THEIR USE AS MEDICAMENTS

The present invention relates to new substituted benzenesulphonic acid esters, processes for their preparation and their use as medicaments, in particular as anthelmintics.

It has already been disclosed that phenylguanidines of the general formula

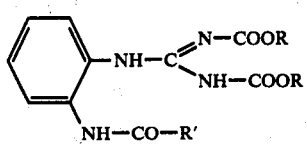

in which
R can denote lower alkyl and
R' can denote both lower alkyl and hydrogen, have anthelmintic actions (for this, see German Offenlegungsschrift (German Published Specification) No. 2,117,293).

However, they have the disadvantage that their anthelmintic action is substantially less strongly pronounced than in the case of the substituted o-phenylenediamine derivatives according to the invention.

It has been found that the new substituted benzenesulphonic acid esters of the formula

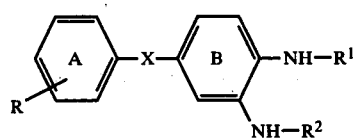

in which
R represents hydrogen, optionally substituted alkyl, cyano, alkoxy, halogen, trifluoromethyl, amino, acylamino or nitro,
X represents $SO_3$ and
$R^1$ and $R^2$ are different from one another and individually represent one of the radicals

wherein
Y represents S and
$R^3$ represents hydrogen, optionally substituted alkyl or alkoxy,
and salts thereof.

The compounds of the invention (i.e. the compounds of the formula (I) and their salts) exhibit a good anthelmintic action. Consequently, of those compounds of the invention which are salts, the pharmaceutically acceptable salts are most important and preferred.

A resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroacemic, phenylacetic, benzoic, 4-aminobenzoic, anthranilic, 4-hydroxybenzoic, salicyclic, aminosalicyclic, embonic, nicotinic, methanesulfonic, ethansulfonic, hydroxyethanesulfonic, ethylenesulfonic, benzenesulfonic, halogenbenzenesulfonic, toluenesulfonic, naphthalenesulfonic and sulfanilic acid; methionine, tryptophan, lysine and arginine.

These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

Furthermore, it has been found that substituted benzenesulphonic acid esters of the formula (I) in which one of the radicals $R^1$ or $R^2$ represents the group

are obtained when phenylamino compounds of the formula (II)

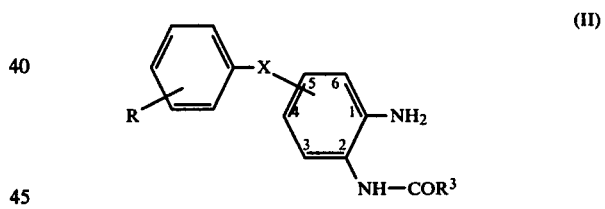

are reacted with methoxycarbonyl isothiocyanate by methods which are in themselves known (reaction variant b).

For convenience, the structural formulae of these compounds used in this specification are those of a single one of the tautomeric forms. However these formula are to be construed as including all tautomeric forms of the compounds.

When the grouping $X=SO_3$ is written in the manner $O-SO_2$ or $SO_2-O$ in the formulae of the present specification and claims it is intended to express that the oxygen atom of the $SO_3$ group is bonded to the phenyl nucleus A and the sulphur atom is bonded to the phenyl nucleus B in the formula I and, in the other case, the oxygen atom of $SO_3$ is bonded to the phenyl nucleus B and the sulphur atom of the $SO_3$ group is bonded to the phenyl nucleus A.

If methoxycarbonyl isothiocyanate and 2-amino-4-phenylsulphonyloxy-acetanilide are used as the starting materials, the course of the reaction can be represented by the following equation:

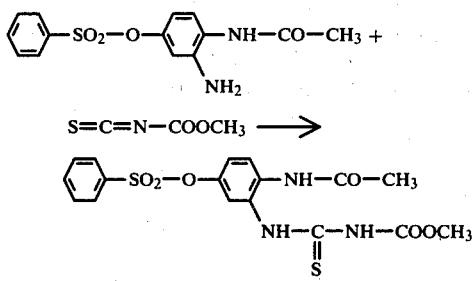

When R in the formula (I) represents optionally substituted alkyl, it is preferably a straight-chain or branched alkyl with 1 to 6, especially 1 to 4, carbon atoms, it being possible for the alkyl part to be substituted by alkoxy ($C_1$–$C_4$) or alkylmercapto ($C_1$–$C_4$), halogen, such as chlorine, fluorine or bromine, or CN. Examples which may be mentioned are the methyl, ethyl, propyl, butyl, methoxymethyl, ethoxymethyl, methoxyethyl, ethoxyethyl, methylmercaptomethyl, methylmercaptoethyl, ethylmercaptoethyl, methylmercaptopropyl, chloromethyl, chloroethyl, trifluoromethyl, cyanomethyl and cyanoethyl group.

When R in the formula (I) represents acylamino it is preferably alkanoylamino, such as having 1 to 7 carbon atoms, such a formylamino, acetylamino, n-propionylamino, i-butyrylamino or n-butyrylamino.

When $R^3$ in the formula (I) represents optionally substituted alkyl it is preferably straight-chain or branched alkyl with 1 to 6, especially 1 to 4, carbon atoms. Examples which may be mentioned are optionally substituted methyl, ethyl, n- and i-propyl and n-, i- and t-butyl.

Possible substituents which may be mentioned for the optionally substituted alkyl radical $R^3$ are: alkoxy ($C_1$–$C_6$), halogen, alkylmercapto ($C_1$–$C_4$) and cyano, and furthermore a radical of the formula

in which
  $R^5$ and $R^6$ can be identical or different and represent hydrogen or alkyl ($C_1$–$C_4$) which is optionally substituted by alkoxy, ($C_1$–$C_4$) trifluoromethyl or cyano,
or in which
  the two radicals $R^5$ and $R^6$, together with the nitrogen atom, form a 5-membered, 6-membered or 7-membered heterocyclic ring which can be interrupted by further hetero-atoms (such as N, O and S) and can be saturated or unsaturated.
Examples of the radical

which may be mentioned are: dimethylamino, diethylamino, dipropylamino, pyrrolidinyl, piperidino and hexamethyleneimino and examples of an interruption of the ring by a further hetero-atom, such as N, O and S, which may be mentioned are morpholino, thiomorpholino, piperazino and N-methylpiperazino.

Examples of further individual substituted alkyl radicals $R^3$ which may be mentioned are: dimethylaminomethyl, dimethylaminoethyl, diethylaminomethyl, diethylaminoethyl, pyrrolidinomethyl, pyrrolidinoethyl, pyrrolidinopropyl, piperidinomethyl, piperidinoethyl, hexamethyleneiminomethyl, hexamethyleneiminoethyl, morpholinomethyl, morpholinoethyl, morpholinopropyl, thiomorpholinoethyl, piperazinomethyl, piperazinoethyl, N-methylpiperazinoethyl, methoxymethyl, ethoxymethyl, propoxymethyl, i-propoxymethyl, methoxyethyl, methoxypropyl, ethoxyethyl, methylmercaptomethyl, ethylmercaptomethyl and ethylmercaptoethyl.

Some of the substituted phenylamino compounds of the formula (II) used as starting materials are not yet known. However, they can be easily prepared analogously to processes which are known from the literature. Thus, for example, 2-amino-4-phenylsulphonyloxy-acetanilide is obtained by the following reaction sequence:

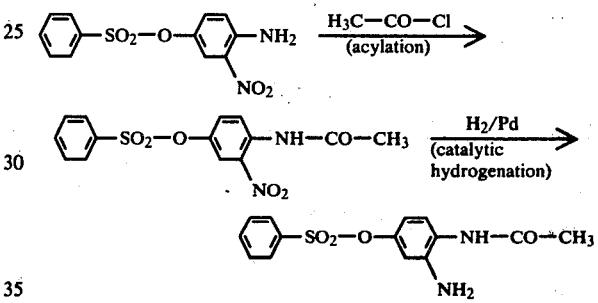

Any inert polar organic solvent is suitable for use as a diluent when carrying out reaction variants (a) and (b).

Preferred solvents include alcohols, such as methanol, ethanol, iso-propanol and mixtures thereof with water, ketones, such as acetone (also mixed with water), and also water-ethers, such as dioxane or tetrahydrofurane. In principle, any of the known organic or inorganic acids may be added in reaction variant (a) as catalysts which promote the reaction. However, the easily accessible, industrially important representatives of these classes are advantageously used. Examples which may be mentioned are: hydrochloric acid, sulphuric acid, nitric acid, formic acid, acetic acid and p-toluenesulphonic acid.

The reaction temperatures can be varied within a wide range. In general, the reaction is carried out between 0° and about 120° C., preferably between 0° and about 80° C. In general, the reaction is carried out under normal pressure in both reaction variants.

Equimolar amounts of the reactants (compounds of the formula (II) and methoxycarbonyl isothiocyanate) are preferably employed when carrying out the reaction according to reaction variant (b).

The preparation of the physiologically acceptable salts can be carried out, using the purified and optionally already recrystallised compounds of the formula (I), by methods which are in themselves known by adding a corresponding amount of a suitable acid, or in solution by precipitating the salts in organic solvents and washing out these salts with inert solvents.

The new compounds can be administered orally and, if they carry a basic centre, also parenterally, those carrying a basic centre also being used in the form of their physiologically acceptable salts, such as, for example, hydrohalides, preferably hydrochlorides, sulphates, phosphates, nitrates, maleates, fumarates, pemoates, acetates, methanesulphonates, naphthalene-disulphonates and others.

The compounds prepared according to the invention exhibit a surprisingly good and broad action in a range from 0.1 to 20 mg/kg of body weight in various individuals, against the following nematodes and cestodes:

1. Hookworms (for example *Uncinaria stenocephala, Ancylostoma caninum* and *Bunostomun trigonocephalum*)
2. Trichostronglidae (for example *Nippostrongylus muris, Haemonchus contortus, Trichostrongylus colubriformis* and *Ostertagia circumcincta*)
3. Strongylidae (for example *Oesophagostomum columbianum*)
4. Rhabditidae (for example *Strongyloides ratti*)
5. Maw-worms (for example *Ascaris suum, Toxocara canis* and *Toxascaris leonina*)
6. Pin-worms (for example *Aspiculuris tetraptera*)
7. Heterakidae (for example *Heterakis spumosa*)
8. Whip-worms (for example *Trichuris muris*)
9. Filariae (for example *Litomosoides carinii* and *Dipetalonema witei*)
10. Cestodes (for example *Hymenolepis nana, Taenia pisiformis* and *Echinococcus multilocularis*)
11. Trematodes (for example *Fasciola hepatica*)

The action was tested in animal experiments after oral and parenteral administration to test animals heavily infected with parasites. The doses used were tolerated very well by the test animals.

The compounds of the invention can thus be used as anthelmintics.

The present invention therefore also provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile or isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of suspension, solutions and emulsions of the active ingredient in aqueous or non-aqueous diluents syrups, granules or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract; possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are powders can, for example, contain the usual diluents, e.g. lactose, talc, silicic acid, aluminum hydroxide, calcium silicate and polyamide powder or mixtures of these substances.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, the solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention preferably contain about 0.1 to 99.5, more preferably from about 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted, by virtue of their shape or packaging, for medical administration and may be, for example, any of the following: tablets, (including lozenges and granules), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 5 mg to 5 g of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the abovementioned diseases in warm-blooded animals, which comprises administering to the said animals a compound of the invention alone or in admixture with a diluent or in the form of a medicament according to the invention.

It is envisaged that these active compounds will be administered perorally, parenterally (for example intramuscularly, intraperitoneally or intravenously), or rectally preferably orally or parenterally, especially subcutaneously. Preferred pharmaceutical compositions and medicaments are therefore those adapted for oral or parenteral administration.

In general, it has proved advantageous to administer to a warm-blooded animal amounts of about 0.1 to about 50 mg preferably of about 5 to about 25 mg of the new compounds per kg of body weight per day in order to achieve effective results.

Nevertheless, it can at times be necessary to deviate from the amounts mentioned and in particular to do so as a function of the body weight of the test animal or the nature of the method of administration, but also because of the type of animal and its individual behaviour towards the medicament or its type of formulation and the time or interval at which it is administered. Thus it can in some cases suffice to manage with less than the abovementioned minimum amount whilst in other cases the upper limit mentioned must be exceeded. Where larger amounts are administered it can be advisable to divide these into several individual administrations over the course of the day. The general sense of the other comments made above also applies.

The anthelmintic action of the active compounds according to the invention is explained in more detail with the aid of the use examples which follow.

EXAMPLE A

Gastric and intestinal worm test/sheep

Sheep experimentally infected with *Haemonchus contortus* or *Trichostrongylus colubriformis* were treated after the end of the pre-patency period of the parasites. The amount of active compound was administered orally as pure active compound in gelatine capsules.

The degree of action is determined by quantitatively counting the worm eggs excreted with the faeces before and after the treatment.

Complete cessation of the excretion of eggs after the treatment means that the worms have been expelled or have been damaged to the point that they can no longer produce eggs (effective dose).

The active compounds examined and the active dosages (minimum effective dose) can be seen from the Table which follows.

Preparation Examples

EXAMPLE 1

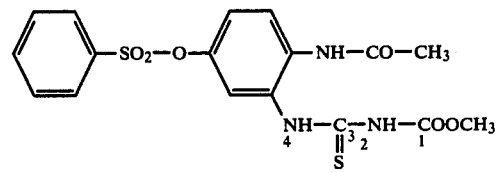

6.05 g of potassium thiocyanate are added to a solution of 15.3 g (0.05 mol) of 2-amino-4-phenylsulphonyloxy-acetanilide in 200 ml of acetone and 4.85 g of chloroformic acid methyl ester, dissolved in 50 ml of acetone, are added dropwise at +5° C. The mixture is stirred for 16 hours at room temperature and gives, after filtering and concentrating in vacuo, 14 g of 4-(2-acetamido-5-phenylsulphonyloxyphenyl)-thioallophanic acid methyl ester of melting point 189° C. (decomposition).

EXAMPLES 2 TO 96

The compounds which follow are obtained from methoxy carbonyl isothiocyanate and 2-amino-4-substituted and 5-substituted anilides by the method described in Example 2:

| Starting materials | Substances prepared according to the invention |
| --- | --- |

-continued

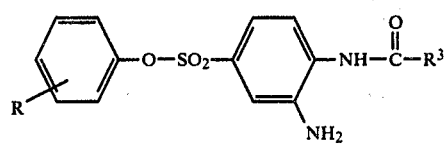 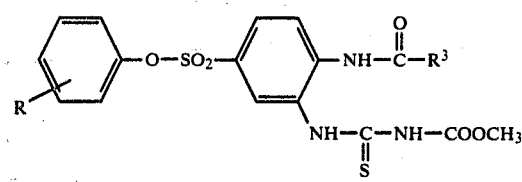

| Ex. No. | R | R³ | Melting point (°C.) | R | R³ | Melting point (°C.) |
|---|---|---|---|---|---|---|
| 2 | H | H | 133–134 | H | H | 196 (decomposition) |
| 3 | H | CH₃ | | H | CH₃ | |
| 4 | H | CH₂—OCH₃ | | H | CH₂—OCH₃ | |
| 5 | H | C₂H₅ | | H | C₂H₅ | |
| 6 | H | C₃H₇ | | H | C₃H₇ | |
| 7 | H | C₄H₉ | | H | C₄H₉ | |
| 8 | H | iso C₄H₉ | | H | iso C₄H₉ | |
| 9 | H | C₅H₁₁ | | H | C₅H₁₁ | |
| 10 | H | CH₂—N(C₂H₅)₂ | | H | CH₂N(C₂H₅)₂ | |
| 11 | H | CH₂—N(CH₃)₂ | | H | CH₂N(CH₃)₂ | |
| 12 | H | CH₂—N(piperidinyl) | | H | CH₂—N(piperidinyl) | |
| 13 | H | CH₂—N(N-methylpiperazinyl) | | H | CH₂—N(N-methylpiperazinyl) | |
| 14 | H | CH₂—SCH₃ | | H | CH₂—SCH₃ | |
| 15 | 3-CF₃ | C₂H₅ | | 3-CF₃ | C₂H₅ | |
| 16 | 3-CF₃ | CH₃ | | 3-CF₃ | CH₃ | |
| 17 | 3-CF₃ | C₃H₇ | | 3-CF₃ | C₃H₇ | |
| 18 | 3-OCH₃ | C₂H₅ | | 3-OCH₃ | C₂H₅ | |
| 19 | 3-CF₃ | H | | 3-CF₃ | H | |
| 20 | 4-CH₃ | C₃H₇ | | 4-CH₃ | C₃H₇ | |
| 21 | 4-NO₂ | C₃H₇ | | 4-NO₂ | C₃H₇ | |
| 22 | 4-NH₂ | C₃H₇ | | 4-NH₂ | C₃H₇ | |
| 23 | 4-CH₃CO—NH | C₂H₅ | | 4-CH₃CO—NH | C₂H₅ | |
| 24 | 4-CN | C₂H₅ | | 4-CN | C₂H₅ | |
| 25 | 3-Cl | C₃H₇ | | 3-Cl | C₃H₇ | |

Starting materials | Substances prepared according to the invention

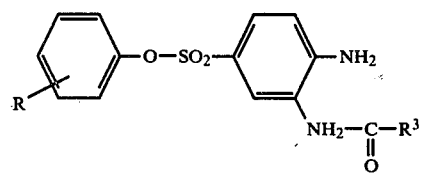 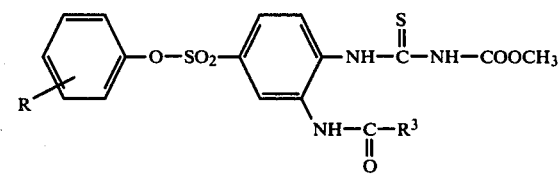

| Ex. No. | R | R³ | Melting point (°C.) | R | R³ | Melting point (°C.) |
|---|---|---|---|---|---|---|
| 26 | H | H | | H | H | |
| 27 | H | CH₃ | | H | CH₃ | |
| 28 | H | CH₂—OCH₃ | | H | CH₂—OCH₃ | |
| 29 | H | C₂H₅ | | H | C₂H₅ | |
| 30 | H | C₃H₇ | | H | C₃H₇ | |
| 31 | H | C₄H₉ | | H | C₄H₉ | |
| 32 | H | iso C₄H₉ | | H | iso C₄H₉ | |
| 33 | H | C₅H₁₁ | | H | C₅H₁₁ | |
| 34 | H | CH₂—N(C₂H₅)₂ | | H | CH₂N(C₂H₅)₂ | |
| 35 | H | CH₂—N(CH₃)₂ | | H | CH₂N(CH₃)₂ | |
| 36 | H | CH₂—N(piperidinyl) | | H | CH₂—N(piperidinyl) | |
| 37 | H | CH₂—N(N-methylpiperazinyl) | | H | CH₂—N(N-methylpiperazinyl) | |
| 38 | H | CH₂—SCH₃ | | H | CH₂—SCH₃ | |
| 39 | 3-CF₃ | C₂H₅ | | 3-CF₃ | C₂H₅ | |
| 40 | 3-CF₃ | CH₃ | | 3-CF₃ | CH₃ | |

-continued

| | | | | | |
|---|---|---|---|---|---|
| 41 | 3-CF₃ | C₃H₇ | | 3-CF₃ | C₃H₇ |
| 42 | 3-OCH₃ | C₂H₅ | | 3-OCH₃ | C₂H₅ |
| 43 | 3-CF₃ | H | | 3-CF₃ | H |
| 44 | 4-CH₃ | C₃H₇ | | 4-CH₃ | C₃H₇ |
| 45 | 4-NO₂ | C₃H₇ | | 4-NO₂ | C₃H₇ |
| 46 | 4-NH₂ | C₃H₇ | | 4-NH₂ | C₃H₇ |
| 47 | 4-CH₃CO—NH | C₂H₅ | | 4-CH₃CO—NH | C₂H₅ |
| 48 | 4-CN | C₂H₅ | | 4-CN | C₂H₅ |

Starting materials

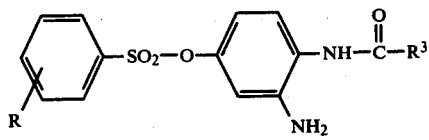

Substances prepared according to the invention

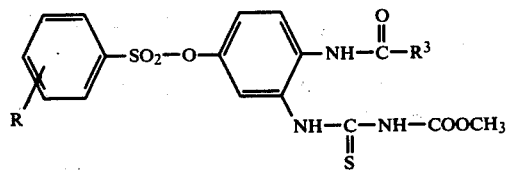

| Ex. No. | R | R³ | Melting point (°C.) | R | R³ | Melting point (°C.) |
|---|---|---|---|---|---|---|
| 49 | H | H | | H | H | |
| 50 | H | CH₃ | | H | CH₃ | |
| 51 | H | CH₂—OCH₃ | | H | CH₂—OCH₃ | |
| 52 | H | C₂H₅ | | H | C₂H₅ | |
| 53 | H | C₃H₇ | | H | C₃H₇ | |
| 54 | H | C₄H₉ | | H | C₄H₉ | |
| 55 | H | iso C₄H₉ | | H | iso C₄H₉ | |
| 56 | H | C₅H₁₁ | | H | C₅H₁₁ | |
| 57 | H | CH₂—N(C₂H₅)₂ | | H | CH₂N(C₂H₅)₂ | |
| 58 | H | CH₂—N(CH₃)₂ | | H | CH₂N(CH₃)₂ | |
| 59 | H | CH₂—N(piperidine) | | H | CH₂—N(piperidine) | |
| 60 | H | CH₂—N(N-methylpiperazine) | | H | CH₂—N(N-methylpiperazine) | |
| 61 | H | CH₂—SCH₃ | | H | CH₂—SCH₃ | |
| 62 | 3-CF₃ | C₂H₅ | | 3-CF₃ | C₂H₅ | |
| 63 | 3-CF₃ | CH₃ | 103 | 3-CF₃ | CH₃ | 165 (decomposition) |
| 64 | 3-CF₃ | C₃H₇ | | 3-CF₃ | C₃H₇ | |
| 65 | 3-OCH₃ | C₂H₅ | | 3-OCH₃ | C₂H₅ | |
| 66 | 3-CF₃ | H | | 3-CF₃ | H | |
| 67 | 4-CH₃ | C₃H₇ | | 4-CH₃ | C₃H₇ | |
| 68 | 4-NO₂ | C₃H₇ | | 4-NO₂ | C₃H₇ | |
| 69 | 4-NH₂ | C₃H₇ | | 4-NH₂ | C₃H₇ | |
| 70 | 4-CH₃CO—NH | C₂H₅ | | 4-CH₃CO—NH | C₂H₅ | |
| 71 | 4-CN | C₂H₅ | | 4-CN | C₂H₅ | |
| 72 | 3-Cl | C₃H₇ | | 3-Cl | C₃H₇ | |
| 73 | 3-CH₃CO—NH | C₃H₇ | | 3-CH₃CO—NH | C₃H₇ | |

Starting materials

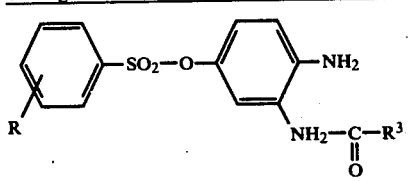

Substances preprared according to the invention

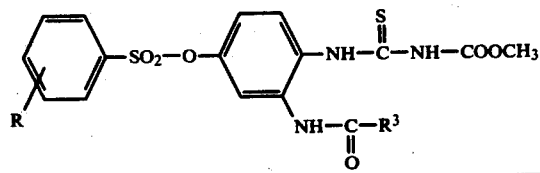

| Ex. No. | R | R³ | Melting point (°C.) | R | R³ | Melting point (°C.) |
|---|---|---|---|---|---|---|
| 74 | H | H | | H | H | |
| 75 | H | CH₃ | | H | CH₃ | |
| 76 | H | CH₂—OCH₃ | | H | CH₂—OCH₃ | |
| 77 | H | C₂H₅ | | H | C₂H₅ | |
| 78 | H | C₃H₇ | | H | C₃H₇ | |
| 79 | H | C₄H₉ | | H | C₄H₉ | |
| 80 | H | iso C₄H₉ | | H | iso C₄H₉ | |
| 81 | H | C₅H₁₁ | | H | C₅H₁₁ | |
| 82 | H | CH₂—N(C₂H₅)₂ | | H | CH₂N(C₂H₅)₂ | |
| 83 | H | CH₂—N(CH₃)₂ | | H | CH₂N(CH₃)₂ | |

-continued

| | | | | |
|---|---|---|---|---|
| 84 | H | CH$_2$—N(piperidine) | H | CH$_2$—N(piperidine) |
| 85 | H | CH$_2$—N(N-methylpiperazine) | H | CH$_2$—N(N-methylpiperazine) |
| 86 | H | CH$_2$—SCH$_3$ | H | CH$_2$—SCH$_3$ |
| 87 | 3-CF$_3$ | C$_2$H$_5$ | 3-CF$_3$ | C$_2$H$_5$ |
| 88 | 3-CF$_3$ | CH$_3$ | 3-CF$_3$ | CH$_3$ |
| 89 | 3-CF$_3$ | C$_3$H$_7$ | 3-CF$_3$ | C$_3$H$_7$ |
| 90 | 3-OCH$_3$ | C$_2$H$_5$ | 3-OCH$_3$ | C$_2$H$_5$ |
| 91 | 3-CF$_3$ | H | 3-CF$_3$ | H |
| 92 | 4-CH$_3$ | C$_3$H$_7$ | 4-CH$_3$ | C$_3$H$_7$ |
| 93 | 4-NO$_2$ | C$_3$H$_7$ | 4-NO$_2$ | C$_3$H$_7$ |
| 94 | 4-NH$_2$ | C$_3$H$_7$ | 4-NH$_2$ | C$_3$H$_7$ |
| 95 | 4-CH$_3$CO—NH | C$_2$H$_5$ | 4-CH$_3$CO—NH | C$_2$H$_5$ |
| 96 | 4-CN | C$_2$H$_5$ | 4-CN | C$_2$H$_5$ |

EXAMPLES FOR THE MANUFACTURE OF COMPOSITIONS

EXAMPLE C 1

A formulation having the following composition is prepared:
(A) N-(2-Acetamido-5-phenylsulfonyloxy-phenyl)-thioallophanic acid methyl ester: 50.0%
(B) Lecithin: 1.5%
(C) Polyoxyethylenesorbitantrioleate: 2.0%
(D) Polyethyleneglycol-laurylether (stabilizer): 2.0%
(E) Mineral Oil: 43.5%

This formulation is prepared by mixing the components B to E and adding component A by stirring until a uniform dispersion is completed.

EXAMPLE C 2

A suspension having the following formulation is prepared:
(A) The formulation of example C 1: 10 g
(B) Polyoxyethylenesorbitantrioleate: 4 g
(C) Polyethyleneglycol-laurylether (stabilizer): 4 g
(D) Oleum Arachidoni: 70 g This formulation is prepared by mixing and stirring the components until it is a uniform dispersion is completed.

EXAMPLE C 3

A formulation having the following composition is prepared:
(A) N-(2-Acetamiodo-5-phenylsulfonyloxy)-phenyl)-thioallophanic acid methyl ester: 30%
(B) Polyethylenglycol 6000: 40%
(C) (Polyoxy (40) stearate): 30%

The components Polyethyleneglycol 6000 and Polyoxy (40) stearate are mixed at 50°-60° C. and then component A is added by stirring. The formulation is solidified by cooling and ground, without remelting of the polyethylene glycol, to a fine powder.

EXAMPLE C 4

A drenchpowder having the following composition is prepared:
(A) The formulation of example C 3: 15 g
(B) colloidal silica: 6 g
(C) Carboxymethylcellulose: 6 g The components are blended together until uniform and then are finely powdered.

EXAMPLE C 5

A suspension having the following formulation is prepared:
(A) The formulation of example C 3: 7.5 g
(B) citric acid, hydrous: 0.43 g
(C) sodium citrat: 0.67 g
(D) carboxymethylcellulose: 1.1 g
(E) colloidal silica: 1 g
(F) sorbic acid: 0.3 g
(G) purified water: to 100 ml The sorbic acid, citric acid and sodium citrate are added to 90 ml of water which has been heated to 80° C. The colloidal silica and carboxymethyl cellulose are then added, with stirring until uniformly dispersed and fully hydrated. The mixture is cooled to 45° C. and the formulation of Example 3 is added, with stirring, until it is uniformly dispersed. The suspension is cooled to room temperature and the balance of the water is added.

What we claim is:

1. A substituted benzenesulphonic acid ester of the formula $$\underset{R}{\text{A}}-X-\underset{NH-R^2}{\overset{NH-R^1}{\text{B}}} \tag{I}$$

in which
R represents hydrogen, a straight-chain or branched alkyl radical with 1 to 6 carbon atoms, unsubstituted or substituted by (C$_1$-C$_4$)-alkoxy, (C$_1$-C$_4$)-alkylmercapto, halogen or CN; or a formylamino, acetylamino, n-propionylamino, i-butrylamino or n-butyrylamino radical,
X represents the group SO$_3$ and
R$^1$ and R$^2$ are different from one another and individually represent one of the radicals $$\overset{Y}{\underset{\|}{C}}-NH-COOCH_3 \text{ and } COR^3$$

wherein
Y represents S and

R³ represents hydrogen, a straight-chain or branched alkyl radical with 1 to 6 carbon atoms, unsubstituted or substituted by (C₁-C₆)-alkoxy, halogen, (C₁-C₄)-alkylmercapto or cyano, or a pharmaceutically acceptable salt thereof.

2. A compound according to claim 1 having formula

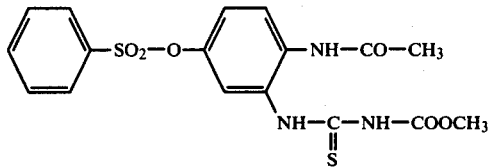

3. A compound according to claim 1 having formula

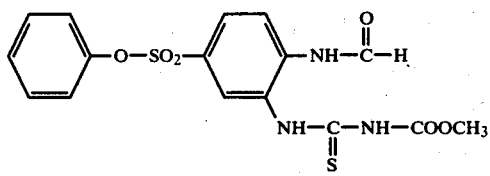

4. A pharmaceutical composition containing as an active ingredient an anthelmintically effective amount of a compound of a substituted benzenesulphonic ester of the formula

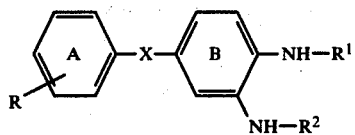

in which
R represents hydrogen, a straight-chain or branched alkyl radical with 1 to 6 carbon atoms, unsubstituted or substituted by (C₁-C₄)-alkoxy, (C₁-C₄)alkylmercapto halogen or CN, or a formylamino, acetylamino, n-propionylamino, i-butrylamino or n-butyrylamino radical, X represents the group SO₃ and R¹ and R² are different from one another and individually represent one of the radicals

wherein
Y represents S and
R³ represents hydrogen, a straight-chain or branched alkyl radical with 1 to 6 carbon atoms, unsubstituted or substituted by (C₁-C₆)-alkoxy, halogen, (C₁-C₄)-alkylmercapto or cyano, or a pharmaceutically acceptable salt thereof;
in admixture with a solid or liquefied gaseous diluent.

5. A pharmaceutical composition containing as an active ingredient an anthelmintically effective amount of a compound of claim 4 in the form of a sterile or isotonic aqueous solution.

6. A composition of claim 4 containing from 0.5 to 95% by weight of the said active ingredient.

7. A composition of claim 5 containing from 0.5 to 95% by weight of the said active ingredient.

8. A medicament in dosage unit form comprising an anthelmintically effective amount of a compound of claim 4 together with an inert pharmaceutical carrier.

9. A medicament of claim 8 in the form of tablets, pills, dragees, capsules, ampoules, or suppositories.

10. A method of combating helminthiases in warm-blooded animals which comprises administering to the said animals an anthelmintically effective amount of an active compound of claim 4 either alone or in admixture with a diluent or in the form of a medicament.

11. A method according to claim 10 in which the active compound is administered in an amount of 0.1 to 50 mg per kg body weight per day.

12. A method according to claim 10 in which the active compound is administered orally.

13. A method according to claim 10 in which the active compound is administered parenterally.

* * * * *